United States Patent
You et al.

(10) Patent No.: US 11,607,287 B2
(45) Date of Patent: Mar. 21, 2023

(54) METHOD OF OPERATING A SURGICAL MICROSCOPE AND SURGICAL MICROSCOPE

(71) Applicant: Carl Zeiss Meditec AG, Jena (DE)

(72) Inventors: Fang You, Aalen (DE); David Dobbelstein, Ulm (DE); Stefan Saur, Aalen (DE)

(73) Assignee: Carl Zeiss Meditec AG, Jena (DE)

( * ) Notice: Subject to any disclaimer, the term of this patent is extended or adjusted under 35 U.S.C. 154(b) by 608 days.

(21) Appl. No.: 16/732,195

(22) Filed: Dec. 31, 2019

(65) Prior Publication Data
US 2021/0196422 A1    Jul. 1, 2021

(51) Int. Cl.
| | |
|---|---|
| A61B 90/25 | (2016.01) |
| G02B 21/00 | (2006.01) |
| G02B 21/22 | (2006.01) |
| A61B 90/00 | (2016.01) |
| A61B 90/50 | (2016.01) |

(52) U.S. Cl.
CPC ............ *A61B 90/25* (2016.02); *A61B 90/361* (2016.02); *A61B 90/50* (2016.02); *G02B 21/0012* (2013.01); *G02B 21/22* (2013.01); *A61B 2090/371* (2016.02); *A61B 2090/502* (2016.02)

(58) Field of Classification Search
CPC ........ A61B 2090/371; A61B 2090/502; A61B 90/25; A61B 90/361; A61B 90/50; G02B 21/0012; G02B 21/22
See application file for complete search history.

(56) References Cited

U.S. PATENT DOCUMENTS

| | | | |
|---|---|---|---|
| 5,641,288 A | 6/1997 | Zaenglein, Jr. | |
| 5,825,982 A * | 10/1998 | Wright | G06F 3/0386 |
| | | | 600/118 |
| 6,459,926 B1 | 10/2002 | Nowlin et al. | |
| 7,190,513 B2 | 3/2007 | Obrebski et al. | |

(Continued)

FOREIGN PATENT DOCUMENTS

| | | |
|---|---|---|
| WO | 2015151447 A1 | 10/2015 |
| WO | 2018078470 A1 | 5/2018 |

OTHER PUBLICATIONS

U.S. Appl. No. 16/732,126, filed Dec. 31, 2019, Fang You et al., Carl Zeiss Meditec AG.

(Continued)

*Primary Examiner* — Mainul Hasan
(74) *Attorney, Agent, or Firm* — Ewers IP Law PLLC; Falk Ewers

(57) ABSTRACT

A method of operating a surgical microscope includes detecting a position of a user, and setting a rotation angle of a camera about its main axis such that it is between a first angle and a second angle. The first angle is the rotation angle required to display a first straight object as a vertical line, and the second angle is the rotation angle required to display a second straight object as a horizontal line. The first object extends along a first line arranged in a vertical plane containing a line connecting the position of the user with the field of view. The first line is horizontal and traverses the field of view. The second object extends along a second line traversing the field of view. The second line is horizontal and perpendicular to the first line.

12 Claims, 2 Drawing Sheets

(56) References Cited

U.S. PATENT DOCUMENTS

| | | | |
|---|---|---|---|
| 2004/0036962 A1* | 2/2004 | Brunner | G02B 21/0012 |
| | | | 359/368 |
| 2006/0028400 A1 | 2/2006 | Lapstun et al. | |
| 2009/0190209 A1* | 7/2009 | Nakamura | G02B 21/361 |
| | | | 359/375 |
| 2012/0307027 A1* | 12/2012 | Popovic | B25J 9/1697 |
| | | | 901/46 |
| 2013/0063580 A1 | 3/2013 | Ogawa et al. | |
| 2014/0049632 A1 | 2/2014 | Hemmer | |
| 2014/0163359 A1 | 6/2014 | Sholev et al. | |
| 2014/0275760 A1 | 9/2014 | Lee et al. | |
| 2014/0303643 A1 | 10/2014 | Ha et al. | |
| 2016/0170488 A1 | 6/2016 | Hanamoto | |
| 2016/0225192 A1 | 8/2016 | Yarin et al. | |
| 2017/0059871 A1 | 3/2017 | Hashiba et al. | |
| 2017/0068081 A1 | 3/2017 | Hirayama | |
| 2017/0115736 A1 | 4/2017 | Patel et al. | |
| 2017/0143442 A1* | 5/2017 | Tesar | A61B 90/37 |
| 2018/0204380 A1 | 7/2018 | Kumar et al. | |
| 2018/0232050 A1 | 8/2018 | Ofek et al. | |
| 2018/0338813 A1 | 11/2018 | Taguchi | |
| 2018/0356880 A1 | 12/2018 | Kashihara | |
| 2019/0008595 A1* | 1/2019 | Popovic | A61B 34/20 |
| 2019/0029765 A1 | 1/2019 | Crawford et al. | |
| 2019/0294103 A1 | 9/2019 | Hauger et al. | |
| 2019/0327394 A1* | 10/2019 | Ramirez Luna | H04N 5/23299 |
| 2019/0328464 A1 | 10/2019 | Saur et al. | |
| 2019/0353457 A1 | 11/2019 | Northrup | |
| 2020/0008899 A1 | 1/2020 | Tripathi et al. | |
| 2021/0186624 A1* | 6/2021 | Charles | A61B 5/1127 |
| 2021/0196396 A1 | 7/2021 | You et al. | |
| 2021/0199940 A1 | 7/2021 | You et al. | |
| 2021/0349303 A1 | 11/2021 | Koch et al. | |
| 2022/0035155 A1 | 2/2022 | Williams et al. | |

OTHER PUBLICATIONS

U.S. Appl. No. 16/732,162, filed Dec. 31, 2019, Fang You et al., Carl Zeiss Meditec AG.

U.S. Appl. No. 16/732,218, filed Dec. 31, 2019, Fang You et al., Carl Zeiss Meditec AG.

* cited by examiner

METHOD OF OPERATING A SURGICAL MICROSCOPE AND SURGICAL MICROSCOPE

CROSS REFERENCE TO RELATED APPLICATIONS

This application relates to U.S. patent application Ser. Nos. 16/732,126, 16/732,162, and 16/732,218, filed on Dec. 31, 2019, the entire contents of which are incorporated herein by reference.

TECHNICAL FIELD

The present disclosure relates to surgical microscopes and methods of operating such surgical microscopes.

BACKGROUND

Conventional surgical microscopes include a microscope body including microscopy optics having two oculars. The microscope body is carried by a support having an articulating structure such that the microscopy optics can be positioned and repositioned relative to an object by translatory and rotatory movements. These movements are initiated by the user looking into the oculars by applying a force to the microscope body using his hands, for example. Such surgical microscopes require the user to permanently look into the oculars which is fatiguing and may create pain, for example, in the neck of the user. Moreover, the user requiring his hands for repositioning the microscope has to lay aside the currently used surgical tool to the effect that the flow of the surgery is interrupted.

Newer surgical microscopes include a camera for recording images of the object under surgery, and a display for displaying the recorded images to the user of the microscope. The user can perform the surgery assuming a convenient position of the head and watch the images on the display since looking into oculars is no longer required. Moreover, the support of these microscopes may include actuators for positioning the articulated joints of the support such that the camera is positioned with a desired orientation at a desired location in space. The desired location and orientation can be inputted into the surgical microscope by various means. For example, WO 2015/151447 A1 describes a surgical microscope in which the direction of gaze of the user and movements of the head of the user are detected to determine new positions of the camera. The actuators of the support are then operated to reposition the camera according to the detected direction of gaze and head movements.

The technologies described above offer significant advantages over the conventional surgical microscope having oculars. Still, it has been found that the process of positioning the camera could be improved.

SUMMARY

The present disclosure has been achieved by taking the above considerations into account, and it is an object of the present disclosure to provide a surgical microscope and a method of operating such surgical microscope thereby improving the user experience in operations involving a repositioning of the camera.

According to an aspect of the disclosure, a surgical microscope includes at least one camera configured to record images of an object located within a field of view of the camera, wherein the at least one camera has a main axis traversing a center of the field of view of the camera, a support for the at least one camera, wherein the support includes at least one actuator for positioning the at least one camera relative to the object and for orienting the at least one camera about the main axis, and a display configured to display images recorded by the at least one camera.

According to an aspect of the disclosure, a method of operating a surgical microscope includes detecting a position of a body portion of a user, determining a rotation angle of the at least one camera about the main axis such that the rotation angle is between a first angle and a second angle.

The position of the body portion of the user may be detected in any suitable coordinate system, such as a coordinate system of the at least one camera and a coordinate system of the object, for example. The rotation angle of the at least one camera about the main axis can be determined based on the relative positions of the body portion of the user, the object and the at least one camera. Herein, the positions of the object and of the at least one camera can be known to a controller of the surgical microscope, or they can be separately detected.

For example, the position of the at least one camera relative to the object can be changed using three translatory degrees of freedom and three rotatory degrees of freedom. When using the surgical microscope, the user may select the position of the at least one camera relative to the object such that the images recorded by the at least one camera are recorded from a desired direction, wherein the camera is positioned at a desired distance from the object. Three translatory coordinates of the camera and three rotatory coordinates of the at least one camera can be set to achieve this requirement. For example, X, Y, and Z coordinates and yaw and pitch angles of the camera can be set accordingly. A roll angle of the camera will then be a remaining degree of freedom which can be used further to position the camera relative to the object. The roll angle of the camera corresponds to the orientation of the camera about the main axis.

The inventors have found that a suitable determination and adjustment of the orientation of the camera about the main axis can significantly improve the user experience in certain situations.

The user performs the surgery by watching the operation area and the manipulations by the hand-held surgical tools on the display. Herein, the user receives an optical feedback of his hand motions. Advantageously, this optical feedback corresponds to expectations of the user gained from earlier surgeries and possibly surgeries performed without a surgical microscope. For example, the user may expect that a movement of his hand in the direction which is horizontal and oriented orthogonally to his line of sight can be seen as a corresponding horizontal movement on the display. Similarly, the user may expect that a movement of his hand in the direction which is oriented orthogonally to the above direction and orthogonally to his line of sight can be seen as a corresponding vertical movement on the display. The user will then expect that a movement in the direction oriented horizontally and orthogonally to the direction which is horizontal and oriented orthogonally to his line of sight can also be seen as a corresponding vertical movement on the display. However, horizontal and vertical directions in the user coordinate system are not necessarily horizontal and vertical directions in a coordinate system of the at least one camera. This may result in a visual feedback on the display which does not match with the user's expectations and deteriorate his abilities to successfully perform the surgery. The exemplary embodiment mentioned above allows to select a suitable range of orientations of the camera about the main axis such that the optical feedback perceived by the user watching the display can be improved. This range of orientations is bounded by the first angle and the second angle. These angles can be determined as described below.

It can be helpful for this illustration to define a first mathematical line and a second mathematical line having positions and orientations relative to the field of view of the camera and the body portion of the user as follows: the first line is arranged in a vertical plane containing a line connecting the position of the body portion of the user with a center of the field of view of the camera, wherein the first line is oriented horizontally and traverses the center of the field of view of the camera. The second line is oriented horizontally and perpendicular to the first line and traverses the center of the field of view of the camera.

Now assuming that a first elongated straight object is positioned in the field of view of the camera such that it extends along the first line, and that a second elongated straight object is positioned in the field of view of the at least one camera such that it extends along the second line. The first angle of orientation of the at least one camera can be found by rotating the at least one camera about the main axis until the first straight object is displayed on the display as a vertical line. The second angle of rotation of the at least one camera can be found by rotating the at least one camera about the main axis until the second straight object is visible on the display as a horizontal line. Herein, the orientations corresponding to the first and second angles are selected such that an absolute value of the difference between the first angle and the second angle is less than 180°.

The first and second angles will change if the position of the body portion of the user relative to the object changes and if the position of the at least one camera relative to the object changes. The first and second angles can be determined by experiment for each given position of the body portion of the user relative to the object and for each given position of the at least one camera relative to the object. In such an experiment, the first and second straight objects can be arranged in the field of view of the at least one camera along the first and second lines, respectively, and the first and second angles can be determined as illustrated above. However, the first and second angles can also be determined by calculation if the positions of the body portion of the user and of the at least one camera relative to the object are known. Therefore, the first and second angles can be determined by a controller of the surgical microscope based just on information available to the controller and relating to the positions of the body portion of the user and of the at least one camera relative to the object or field of view of the camera. The information relating to the position of the body portion of the user can be obtained using a suitable sensor. The information relating to the position of the at least one camera relative to the object or body portion of the user can be obtained using a suitable sensor or based on a known geometry of the support and states of the actuators controlled by such controller.

Depending on the relative positions of the body portion of the user and the at least one camera relative to the object, there can be situations in which there is no difference between the first and second angles determined as illustrated above. However, in other situations, this difference can be significant. The absolute value between the first angle and second angle can be larger than 5°, 10°, or 15°. The inventors have found that, in such situations, an orientation of the at least one camera according to the first angle or the second angle may degrade the user experience, while an orientation of the at least one camera somewhere between the first and second angles can improve the user experience.

According to an aspect of the disclosure, the smaller one of an absolute value of a difference between the first angle and the rotation angle and of an absolute value of a difference between the second angle and the rotation angle is larger than 0.1 times the absolute value of the difference between the first angle and the second angle. This may ensure a sufficient difference from orientations corresponding to exactly the first or second angle in order to achieve an improvement of the user experience.

According to an aspect of the disclosure, the absolute value of the difference between the first angle and the rotation angle is equal to the absolute value of the difference between the second angle and the rotation angle.

According to another aspect of the disclosure, the determination of the rotation angle is performed as soon as a change of the position of the body portion of the user is detected. Moreover, the determination of the rotation angle can be performed as soon as the position of the at least one camera relative to the object is changed. In order to avoid permanent changes of the orientation of the at least one camera and of the displayed images, it is possible to apply a smoothing filter, such as a Kalman filter, to the detected positions of the body portion of the user and to determine the rotation angle based on the filtered detected positions of the body portion of the user.

According to an aspect of the disclosure, the camera is a stereo camera configured to record a pair of stereo images. For example, the at least one camera may include two cameras for this purpose.

According to an aspect of the disclosure, the display is configured to display stereoscopic images. According to another aspect of the disclosure, the display is a head-mounted display which can be carried by the user of the surgical microscope. According to yet another aspect of the disclosure, the display includes a screen displaying the images obtained by processing the pair of stereo images, and a pair of glasses wearable by a user and allowing the user to see the displayed images obtained by processing left images of the pairs of stereo images with the left eye and to see the displayed images obtained by processing the right images of the pairs of stereo images with the right eye.

According to an aspect of the disclosure, the surgical microscope includes a controller configured to perform the methods described above.

BRIEF DESCRIPTION OF THE DRAWINGS

The disclosure will now be described with reference to the drawings wherein.

DESCRIPTION OF EXEMPLARY EMBODIMENTS

Figure 1:
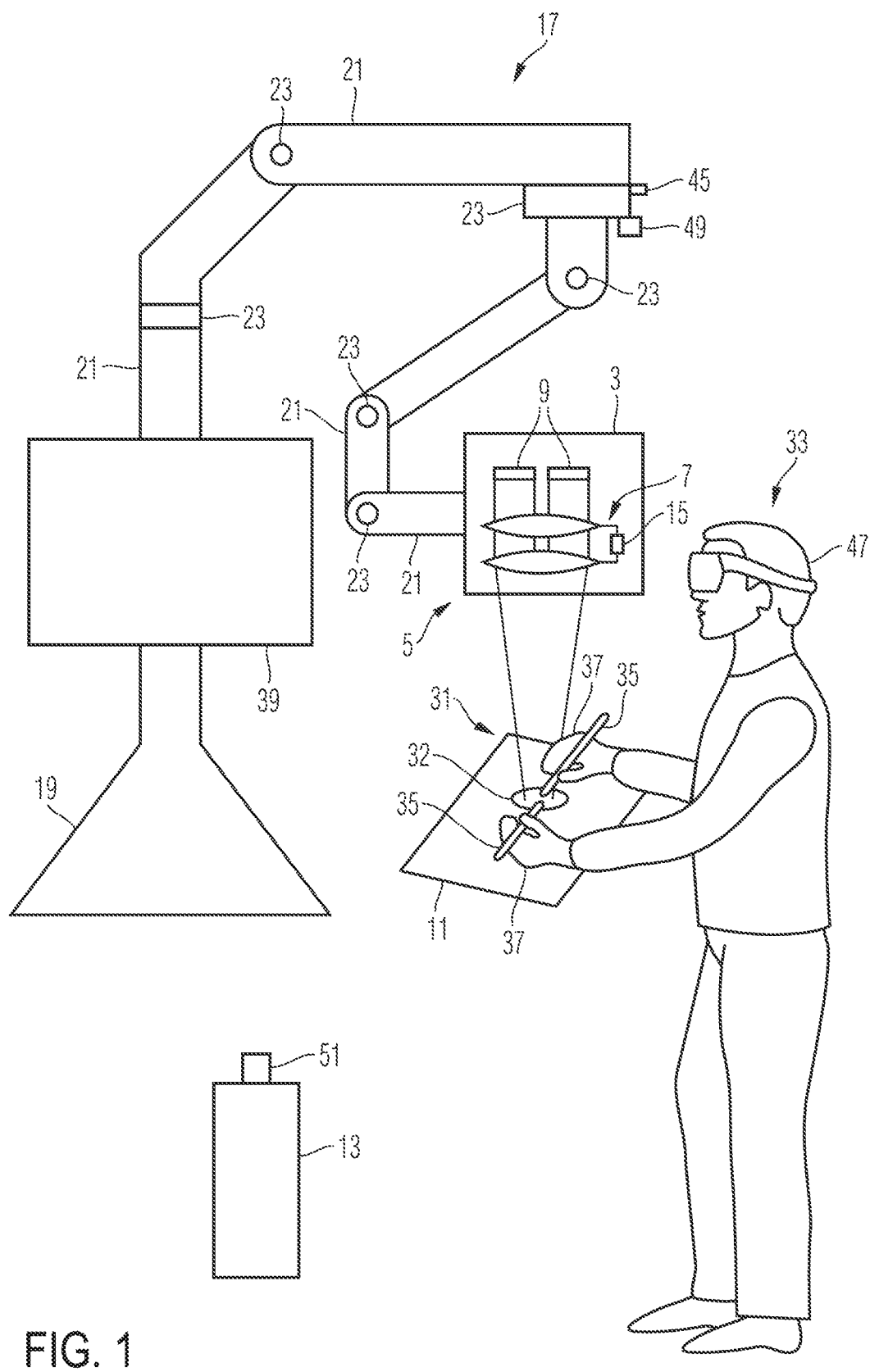
FIG. 1 shows a schematic illustration of a surgical microscope.

The forgoing as well as other advantageous features of the disclosure will be more apparent from the following detailed description of exemplary embodiments with reference to the accompanying drawings. It is noted that not all possible exemplary embodiments necessarily exhibit each and every, or any, of the advantages identified herein.

In the exemplary embodiments described below, components that are alike in function and structure are designated as far as possible by alike reference numerals. Therefore, to understand the features of the individual components of a specific exemplary embodiment, the descriptions of other exemplary embodiments and of the summary of the disclosure should be referred to.

FIG. 1 shows a schematic illustration of a surgical microscope 1. The surgical microscope 1 includes a microscope body 3, a housing, microscopy optics 5 including a magnifying zoom lens 7, and two cameras 9. The cameras 9 record images of a field of view of the cameras 9 in a focal plane 11. The optics 5 is configured to adjust a distance of the focal plane 11 from the microscope body by operating an actuator (not shown in FIG. 1) controlled by a controller 13 of the surgical microscope 1. Images of the field of view of the cameras 9 recorded by the cameras 9 are transmitted to the controller 13. The magnification of an object located in the field of view in the images recorded by the cameras 9 can be adjusted by the controller by operating an actuator 15 of the zoom lens 7.

The microscope body 3 is carried by a support 17 including a base 19 placed on a floor of an operation room, and plural members 21 connected by joints including actuators 23 controlled by the controller 13 in order to position the microscope body 3 within an accessible region of the operation room. The support 17 is configured to be controlled by the controller 13 such that the microscope body 3 performs both translatory movements in three independent directions and rotatory movements about three independent axes. Specifically, the actuators 23 of the support can be operated to position the cameras 9 such that the field of view of the cameras coincides with a surgical area 31 were a user 33 of the surgical microscope 1 performs a surgery with surgical tools 35 held by his hands 37. For this purpose, the user watches the surgical area 31 by looking at a display showing images transmitted from the controller 13. The images displayed on the display can be images obtained by processing the images recorded by the cameras 9. The processing of the images may include any image processing operation, such as cropping, rotating, contrast enhancement, color correction, and direct display of the recorded images without substantial changes to the image data.

The display can be, for example a flat panel display 39 which can be mounted on the support 17, or a head-mounted display 41 carried by the user 33.

The images recorded by the two cameras 9 are pairs of stereo images showing the surgical area from different angles. The pairs of stereo images can be watched by the user using the head-mounted display 41 so that the user 33 perceives a three-dimensional impression of the surgical area. Similarly, also the flat panel display 39 can be configured to display stereo images, wherein the user 33 will wear suitable glasses selecting the displayed images transmitted to the left and right eyes of the user. For example, the flat panel display 39 may alternatingly display the images for the left and right eyes while the glasses are active shutter glasses alternatingly transmitting light to the left and right eyes of the user 33. Moreover, the flat panel display 39 may display the images for the left and right eye of the user simultaneously using different polarization states of pixels of the screen, wherein the user 33 carries corresponding polarizing glasses.

The surgical microscope 1 further includes a sensor 45 allowing the controller to determine a position and orientation of a body portion, such as a head 47 of the user 33, relative to the microscope body 3, relative to the field of view 11 of the cameras 9 or relative to some other suitable position within the operation room. The sensor 45 can be mounted at any suitable position, such as an element of the support 17, on the display, 39 and 41. Moreover, the sensor may include a plurality of sensor elements arranged at a plurality of distributed locations.

The surgical microscope 1 further includes a sensor 49 allowing the controller 13 to determine a direction of gaze of the user 33. Specifically, the controller 13 may determine a position within the images displayed on the display 39 and 41 at which the eyes of the user are directed. Also, the sensor 49 can be mounted at any suitable position, such as an element of the support 17, on the display, 39 and 41. Moreover, the sensor may include a plurality of sensor elements arranged at a plurality of distributed locations.

The surgical microscope 1 further includes a sensor 51 allowing the controller 13 to receive commands issued by the user 33. For example, the sensor 51 may include a switch operated by the user 33 to enter a start command and a stop command. Moreover, the sensor 51 may include a microphone allowing the controller 13 to detect voice commands, such as "start" and "stop".

A method of orienting a camera of a surgical microscope relative to an object will now be described with reference to FIGS. 2 and 3A to 3C.

Figure 2:
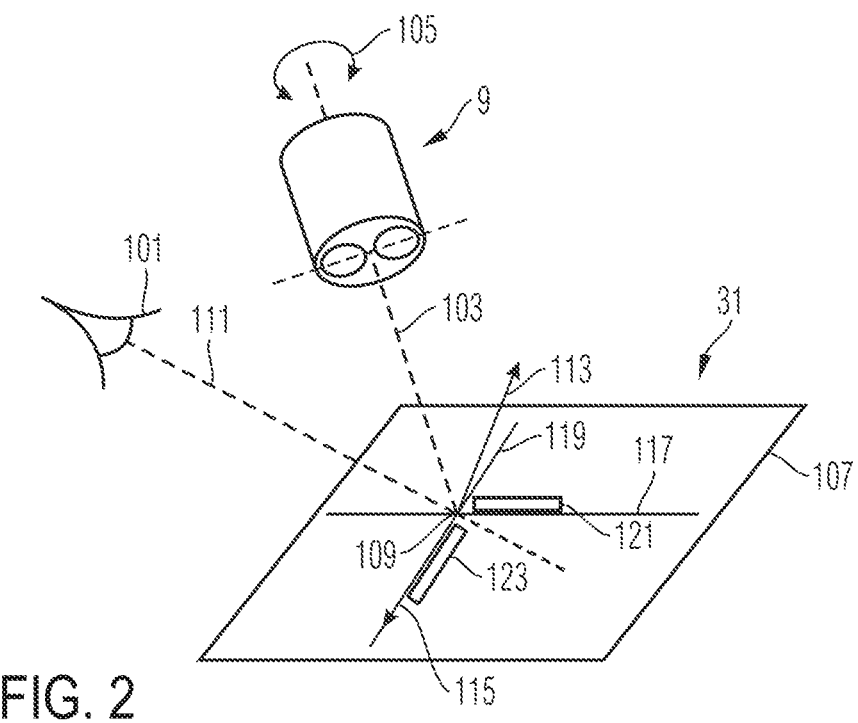
FIG. 2 shows a schematic illustration of geometric relations between the user and the surgical microscope shown in FIG. 1.

FIG. 2 shows geometric relations between a body portion 101 of the user 33, the two cameras 9 and the surgical area 31. The cameras 9 can be rotated about a main axis 103 of the cameras 9 by suitably controlling the actuators 23, as indicated by arrow 105 in FIG. 2. The main axis 103 can be selected such that it intersects a center of the field of view of the cameras 9. Rectangle 107 in FIG. 2 represents a horizontal plane intersecting the focal plane of the cameras and the main axis 103 of the cameras 9 at a point 109. Point 109 is located at a distance from the camera such that the focal plane of the cameras contains point 109. An image of an object located at the point 109 recorded by the cameras 9 is a sharp representation of the object. A line 111 connects the body portion 101 of the user with point 109.

As shown in FIG. 2, the body portion of the user is the user's eye. However, other portions of the body of the user can be used as origins of the line 111. For example, a point between the two eyes of the user or a point between the two shoulders of the user can be selected as an origin of the line 111.

Arrow 113 in FIG. 2 originates from point 109, is contained in a vertical plane containing the line 111 and is oriented upwards and orthogonal to the line 111.

Arrow 115 in FIG. 2 originates from point 109, is contained in the horizontal plane 107 and is perpendicular to both the arrow 113 and the line 111.

From the point of view of the user, the arrow 113 points vertically up, and the arrow 115 points horizontally to the right. From the point of view of the cameras 9, the arrows 113 and 115 are oriented in directions depending on the rotational position of the cameras 9 about the main axis 103. Moreover, from the point of view of the cameras 9, the arrows 113 and 115 may be oriented in directions which are not orthogonal to each other.

A first line 117 in FIG. 2 is contained in a vertical plane containing the line 111 connecting the body portion 101 of the user and the center 109 of the field of view of the cameras 9. Moreover, line 117 traverses the center 109 of the field of view of the cameras 9, and the line 117 is oriented in the horizontal direction. Line 117 is contained in plane 107, accordingly.

Arrow 115 coincides with a second line 119. The second line 119 traverses the center 109 of the field of view of the camera and is oriented horizontally and perpendicular to the first line 117. Also line 119 is contained in the plane 107, accordingly.

FIG. 2 further shows a first elongated straight object 121 and a second elongated straight object 123. The first straight object 121 is arranged along the first line 117 within the field of view of the cameras 9, and the second straight object 123 is arranged along the second line 119 within the field of view of the cameras 9.

Figure 3A:
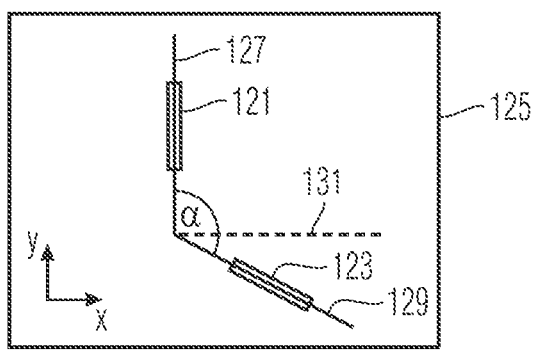
FIGS. 3A to 3C show schematic illustrations of displayed images for different orientations of the cameras shown in FIG. 2.

FIG. 3A shows an image 125 of the first and second objects 121, 123 recorded by the cameras 9 and displayed on the display 39 and 41. While the straight objects 121 and 123 are oriented perpendicular to each other in reality, they appear to extend along lines 127 and 129, respectively in the displayed image 125, wherein the lines 127 and 129 are oriented at an angle α relative to each other which is significantly different from 90°.

For recording the displayed image 125 shown in FIG. 3A, the rotation angle of the cameras 9 about the main axis 103 has been adjusted to a first angle selected such that the line 127 of extension of the image of the first object 121 extends in the vertical direction (y) in the displayed image 125. As a consequence, the second line 129 is not oriented in the horizontal direction (x) in the displayed image 125.

It is apparent that the visual feedback the user receives from a horizontal movement along the line 117 in FIG. 2 conforms to his expectations since a horizontal movement of a tool in the field of view of the cameras along this line 117 results in a vertical movement of this tool on the display 39 and 41. However, a movement of the tool in the horizontal plane 107 along the line 115 results in a movement of the tool along the line 129 on the display which is oriented diagonal in the displayed image 125 of FIG. 3. However, the user would expect that the movement of the tool along the line 115 results in a movement along a horizontal line 131 in the displayed image 125.

Figure 3B:
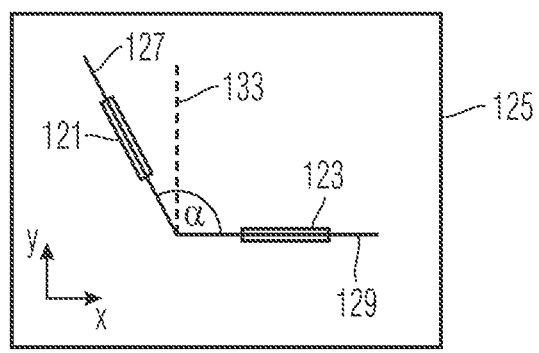

FIG. 3B shows a situation in which the rotation angle of the cameras 9 about the main axis 103 has been adjusted to a second angle selected such that the line 129 of extension of the image of the second object 123 extends in the horizontal direction (x) in the displayed image 125. As a consequence, the first line 129 is not oriented in the vertical direction (y) in the displayed image 125.

In this situation, the visual feedback the user receives from a horizontal movement along the line 115 in FIG. 2 conforms to his expectations since a horizontal movement of a tool in the field of view of the cameras along this line 115 results in a horizontal movement of this tool on the display 39 and 41. However, a movement of the tool in the horizontal plane 107 along the line 117 results in a movement of the tool along the line 127 on the display which is oriented diagonal in the displayed image 125 of FIG. 3. However, the user would expect that the movement of the tool along the line 117 results in a movement along a vertical line 133 in the displayed image 125.

Figure 3C:
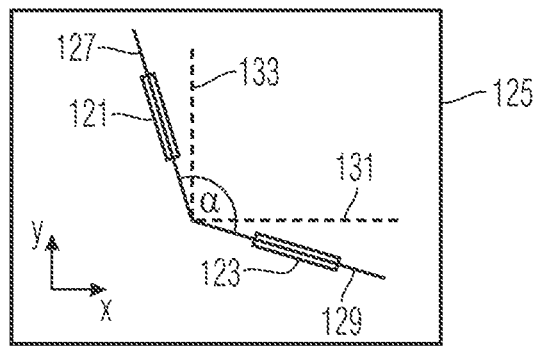

FIG. 3C shows a situation in which the rotation angle of the cameras 9 about the main axis 103 has been adjusted to an advantageous angle selected such that it is between the first and second angles illustrated above. It is apparent that neither the horizontal movement of the tool along the line 117 results in a vertical movement of this tool on the display 39 and 41, nor does the movement of the tool along the line 115 result in a horizontal movement of the tool on the display 39 and 41. However, the maximum of the angle between the vertical line 133 and the line 127 and of the of the angle between the horizontal line 131 and the line 129 in FIG. 3C is significantly smaller than in each of FIGS. 3A and 3C. Therefore, with the selection of the rotation angle according to FIG. 3C, the user experience can be better than in the situations shown in FIGS. 3A and 3C.

While the angle between the vertical line 133 and the line 127 is not exactly equal to the angle between the horizontal line 131 and the line 129 in in the situation shown in FIG. 3C, the rotation angle of the cameras 9 can be selected such that these angles have the same size.

In the exemplary embodiments described above, the rotation of the image to the advantageous orientation shown in FIG. 3C is achieved by a rotation of the cameras. However, it is also possible to generate images having the advantageous orientation by image processing. In a corresponding exemplary embodiment, the camera can be maintained in a given orientation about the axis 103 which is different from the illustrated advantageous orientation. Still, images oriented according to the advantageous orientation can be displayed on the display by processing the recorded images and displaying the processed images, wherein the processing of the images includes an image rotation operation.

While the disclosure has been described with respect to certain exemplary embodiments thereof, it is evident that many alternatives, modifications and variations will be apparent to those skilled in the art. Accordingly, the exemplary embodiments of the disclosure set forth herein are intended to be illustrative and not limiting in any way. Various changes may be made without departing from the spirit and scope of the present disclosure as defined in the following claims.

What is claimed is:

1. A method of operating a surgical microscope, the surgical microscope including at least one camera configured to record images of an object located within a field of view of the at least one camera, the at least one camera having a main axis traversing a center of the field of view of the at least one camera, a support for the at least one camera, the support including at least one actuator for positioning the at least one camera relative to the object and for orienting the at least one camera about the main axis, and a display configured to display the images recorded by the at least one camera, the method comprising:
   detecting a position of a body portion of a user;
   determining a rotation angle of the at least one camera about the main axis such that the rotation angle is between a first angle and a second angle; and
   operating the at least one actuator according to the rotation angle,
   wherein the first angle is the rotation angle of the at least one camera required to display a first straight object, when it is located within the field of view of the at least one camera, as a vertical line on the display,
   wherein the second angle is the rotation angle of the at least one camera required to display a second straight object, when it is located within the field of view of the at least one camera, as a horizontal line on the display,
   wherein a first object extends along a first line,
   wherein the first line is arranged in a vertical plane including a line connecting the position of the body portion of the user with the center of the field of view of the at least one camera,
   wherein the first line traverses the center of the field of view of the at least one camera, wherein the first line is oriented horizontally,
wherein a second object extends along a second line,
wherein the second line traverses the center of the field of view of the at least one camera, and
wherein the second line is oriented horizontally and perpendicular to the first line.

2. The method of claim 1, wherein an absolute value of a difference between the first angle and the second angle is larger than at least one of 5°, 10°, and 15°.

3. The method of claim 1, wherein a smaller one of an absolute value of a difference between the first angle and the rotation angle and of the absolute value of the difference between the second angle and the rotation angle is larger than 0.1 times the absolute value of the difference between the first angle and the second angle.

4. The method of claim 3, wherein the absolute value of the difference between the first angle and a rotation is equal to the absolute value of the difference between the second angle and the rotation angle.

5. The method of one of claim 1, further comprising:
detecting a change in the position of the body portion of the user, and
wherein the determining of the rotation angle is performed in response to a detection of the change in the position of the body portion of the user.

6. The method of claim 1, further comprising:
receiving an instruction to move the at least one camera to new position relative to the object, and
wherein the determining of the rotation angle is performed in response to the receiving of the instruction to move the at least one camera to the new position and based on the field of view of the at least one camera in the new position.

7. The method of one of claim 1, wherein the at least one camera is a stereo camera.

8. The method of claim 1, wherein the surgical microscope includes two cameras.

9. The method of claim 1, wherein the display is configured to display stereoscopic images.

10. The method of claim 9, wherein the display is a head-mounted display.

11. The method of claim 9, wherein the display comprises:
a screen displaying the images obtained by processing the images recorded by a first camera and a second camera of the at least one camera; and
a pair of glasses wearable by the user and allowing the user to see displayed images obtained by processing the images recorded by the first camera with his or her left eye and to see the displayed images obtained by processing the images recorded by the second camera with his or her right eye.

12. The surgical microscope comprising:
the at least one camera configured to record the images of the object located within the field of view of the at least one camera, the at least one camera having the main axis traversing the center of the field of view of the at least one camera;
the support for the at least one camera, the support including the at least one actuator for positioning the at least one camera relative to the object and for orienting the at least one camera about the main axis;
the display configured to display the images recorded by the at least one camera; and
a controller configured to perform the method of claim 1 with the surgical microscope.

* * * * *